(12) United States Patent
Evenhaim

(10) Patent No.: US 7,823,207 B2
(45) Date of Patent: Oct. 26, 2010

(54) PRIVACY PRESERVING DATA-MINING PROTOCOL

(75) Inventor: Asaf Evenhaim, New York, NY (US)

(73) Assignee: Crossix Solutions Inc., New York, NY (US)

(*) Notice: Subject to any disclaimer, the term of this patent is extended or adjusted under 35 U.S.C. 154(b) by 1084 days.

(21) Appl. No.: 10/597,631

(22) PCT Filed: Apr. 1, 2005

(86) PCT No.: PCT/IL2005/000364

§ 371 (c)(1),
(2), (4) Date: Aug. 2, 2006

(87) PCT Pub. No.: WO2005/094175

PCT Pub. Date: Oct. 13, 2005

(65) Prior Publication Data

US 2007/0282796 A1 Dec. 6, 2007

(30) Foreign Application Priority Data

Apr. 2, 2004 (IL) .................................. 161263

(51) Int. Cl.
G06F 17/30 (2006.01)
G06F 21/00 (2006.01)
G06F 12/14 (2006.01)
G06F 7/00 (2006.01)
H04L 29/06 (2006.01)
H04L 9/32 (2006.01)

(52) U.S. Cl. ................... 726/26; 726/2; 726/4; 726/28; 726/29; 726/30; 713/151; 713/161; 713/165; 713/168; 713/182; 713/189; 707/607; 707/609; 707/687; 707/694; 707/705; 707/706; 707/732; 707/752; 707/754; 707/776; 707/781; 707/783; 707/805

(58) Field of Classification Search ................... 726/26, 726/2, 4, 28–30; 713/151, 161, 165, 168, 713/182, 189; 707/607, 609, 687, 694, 705, 707/706, 732, 752, 754, 776, 781, 783, 805
See application file for complete search history.

(56) References Cited

U.S. PATENT DOCUMENTS 4,965,763 A    10/1990 Zamora (Continued)

OTHER PUBLICATIONS

Data Rights Agreement Between Quintiles and Healtheon/WebMD Attached file name: WEBMD-Quintiles Data Sharing Agreement.pdf.

(Continued)

*Primary Examiner*—Aravind K Moorthy
(74) *Attorney, Agent, or Firm*—Galbreath Law Offices, P.C.; John A. Galbreath

(57) ABSTRACT

Privacy Preserving Data-Mining Protocol, between a secure "aggregator" and "sources" having respective access to privacy-sensitive micro-data, the protocol including: the "aggregator" accepting a user query and transmitting a parameter list for that query to the "sources" (often including privacy-problematic identifiable specifics to be analyzed); the "sources" then forming files of privacy-sensitive data-items according to the parameter list and privacy filtering out details particular to less than a predetermined quantity of micro-data-specific data-items; and the "aggregator" merging the privacy-filtered files into a data-warehouse to formulate a privacy-safe response to the user—even though the user may have included privacy-problematic identifiable specifics.

12 Claims, 7 Drawing Sheets

U.S. PATENT DOCUMENTS

| | | | |
|---|---|---|---|
| 5,253,164 | A | 10/1993 | Holloway |
| 5,307,262 | A | 4/1994 | Ertel |
| 5,420,786 | A | 5/1995 | Felthauser |
| 5,491,473 | A | 2/1996 | Gilbert |
| 5,544,044 | A | 8/1996 | Leatherman |
| 5,557,514 | A | 9/1996 | Seare |
| 5,628,530 | A | 5/1997 | Thornton |
| 5,781,893 | A | 7/1998 | Felthauser |
| 5,794,042 | A | 8/1998 | Terada |
| 5,835,897 | A | 11/1998 | Dang |
| 5,845,255 | A | 12/1998 | Mayaud |
| H1782 | H | 2/1999 | Wicks |
| 5,950,630 | A | 9/1999 | Portwood |
| 6,014,631 | A | 1/2000 | Teagarden |
| 6,067,523 | A | 5/2000 | Bair |
| 6,223,164 | B1 | 4/2001 | Seare |
| 6,269,404 | B1 | 7/2001 | Hart |
| 6,305,377 | B1 | 10/2001 | Portwood |
| 6,356,873 | B1 | 3/2002 | Teagarden |
| 6,370,511 | B1 | 4/2002 | Dang |
| 6,397,224 | B1 | 5/2002 | Zubeldia |
| 6,529,952 | B1 | 3/2003 | Blumenau |
| 6,578,003 | B1 | 6/2003 | Camarda |
| 6,584,472 | B2 | 6/2003 | Classen |
| 6,587,829 | B1 | 7/2003 | Camarda |
| 6,611,846 | B1 | 8/2003 | Stoodley |
| 6,636,875 | B1 | 10/2003 | Bashant |
| 7,111,237 | B2 * | 9/2006 | Chan .......................... 715/265 |
| 2004/0260694 | A1 * | 12/2004 | Chaudhuri et al. ............. 707/5 |
| 2005/0004911 | A1 * | 1/2005 | Goldberg et al. ............... 707/7 |

OTHER PUBLICATIONS

Right-Channeling Consumer Drug Marketing by Forrester Research Attached file name: Right Channeling CD Mark.pdf.

Pharmetrics HIPAA Compliance: Statistical Disclosure Limitation Methodology Attached file name: Pharmetrics HIPAA Compliance. pdf.

Pfizer and RxRemedy—the Impact of DTC Advertising Relative to Patient Compliance Attached file name: Pfizer Inc Impact of DTC Advertising.pdf.

MTS HealthTrak Inserts Essential 'Why' in Consumer Rx Purchasing Behaviors and Patterns Attached file name: MTS Healthtrak.pdf.

Using De-Identified Information to Simplify Privacy Compliance Attached file name: Legal review of de-identification.pdf.

Adherence to Long-Term Therapies Evidence for action by the World Health Organization 2003 Attached file name: Adherence report.pdf.

CBI Conference Agenda for Anonymous Patient-Level Data and Analysis, Nov. 2003 Attached file name: CBI Conf. on Patient-Level Data.pdf.

NDC Health Pharmaceutical website, as of Nov. 11, 2003 Attached file name: NDCHealth Pharmaceutical website.pdf.

Tools for Privacy Preserving Distributed Data Mining Attached file name: Tools for Privacy Preserving Distributed Data Mining.pdf.

K-anonymity—A Model for Protecting Privacy Attached file name:K-anonymity—A Model for Protecting Privacy.pdf.

Dataset De-Identification—A Technical Overview Attached file name: Dataset De-Identification—A Technical Overview.pdf.

* cited by examiner

PRIVACY PRESERVING DATA-MINING PROTOCOL

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to data privacy and data usage in distributed database systems—often belonging to disparate owners. More specifically, the present invention relates to coordination of data privileges while simultaneously preserving data privacy and allowing useful facilitation of privacy sensitive data features.

BACKGROUND OF THE INVENTION

The worlds of database coordination, data rights and data usage are inherently paradoxical, since privacy preserving legal rights restrict usage of technical functions in some circumstances while permitting these same technical functions in other circumstances. Simply stated, usage of functions such as sort, search, merge, and Boolean logical operators are the pith and marrow of database operations—except when one of the database fields or a combination of several fields may lead to identification of a person.

Identifiable data may not be from one field and may not be that explicit. For example, a study done on the Census data in the US demonstrated that 87% of US population can be uniquely identified just based on Date-Of-Birth, Sex and ZIP code. There is also the issue of being able to re-identify someone based on an external public database (such as voter registration that includes DOB, Sex and ZIP). So bottom line, the real issue is the level uniqueness of a record and not necessarily a specific field. It is with this very concern in mind that data providers bundle their information goods into identity camouflaged collections or otherwise aggregate records or "trim" down the data to create more "same" records (e.g. report only the first three digits of a ZIP code or report only year of birth)—so that one cannot know, at a certain level of probability, if some particular John Doe is present in one category of an eventual statistical report or any specific details about him; even though this report is based on information goods where John Doe is explicitly labeled, quantitatively described and categorically characterized.

Numerous fields of endeavor come to mind wherein this data privacy paradox prohibits making best use of the information—especially for applications that are not concerned with any particular John Doe. For example, healthcare organizations such as physician practices, labs, hospitals and health maintenance organizations (HMOs) keep extensive medical records including data on each specific patient and on each specific doctor. The Health Insurance Portability and Accountability Act of 1996 (HIPAA) in the USA and similar legislation in other jurisdictions prevents HMOs and healthcare providers from sharing data at full transparency—since the privacy of individuals must be preserved. (see FIGS. 1 & 2 for further details) Nevertheless, without any interest in specific individuals, pharmaceutical companies could greatly improve many technical and mercantile aspects of their operation—if they were given unrestricted access to the HMO raw data. Similar data opacity exists between banks and insurance companies, between sellers of goods and credit card companies, between the census bureau and other government agencies (e.g. tax authorities, public health systems, etc.).

Just for example, the HIPAA related section talking about de-identification says: §164.514 Other requirements relating to uses and disclosures of protected health information.

(a) Standard: de-identification of protected health information. Health information that does not identify an individual and with respect to which there is no reasonable basis to believe that the information can be used to identify an individual is not individually identifiable health information.

(b) Implementation specifications: requirements for de-identification of protected health information. A covered entity may determine that health information is not individually identifiable health information only if:

(1) A person with appropriate knowledge of and experience with generally accepted statistical and scientific principles and methods for rendering information not individually identifiable: (i) Applying such principles and methods, determines that the risk is very small that the information could be used, alone or in combination with other reasonably available information, by an anticipated recipient to identify an individual who is a subject of the information; and (ii) Documents the methods and results of the analysis that justify such determination; or (2)(i) The following identifiers of the individual or of relatives, employers, or household members of the individual, are removed: (A) Names; (B) All geographic subdivisions smaller than a State, including street address, city, county, precinct, zip code, and their equivalent geo-codes, except for the initial three digits of a zip code if, according to the current publicly available data from the Bureau of the Census: (1) The geographic unit formed by combining all zip codes with the same three initial digits contains more than 20,000 people; and (2) The initial three digits of a zip code for all such geographic units containing 20,000 or fewer people is changed to 000. (C) All elements of dates (except year) for dates directly related to an individual, including birth date, admission date, discharge date, date of death; and all ages over 89 and all elements of dates (including year) indicative of such age, except that such ages and elements may be aggregated into a single category of age 90 or older; (D) Telephone numbers; (E) Fax numbers; (F) Electronic mail addresses; (G) Social security numbers; (H) Medical record numbers; (I) Health plan beneficiary numbers; (J) Account numbers; (K) Certificate/license numbers; (L) Vehicle identifiers and serial numbers, including license plate numbers; (M) Device identifiers and serial numbers; (N) Web Universal Resource Locators (URLs); (O) Internet Protocol (IP) address numbers; (P) Biometric identifiers, including finger and voice prints; (Q) Full face photographic images and any comparable images; and (R) Any other unique identifying number, characteristic, or code; and (ii) The covered entity does not have actual knowledge that the information could be used alone or in combination with other information to identify an individual who is a subject of the information.

Again, specifically with reference to a non-limiting example of health care related information systems—it is worthy to note some additional Background Factors:

(A) The rising cost of health care—Health care expenses and utilization are growing at an alarming, unprecedented rate. In 2000 Americans spent $1.3 trillion on health care. That's more than was spent on food, housing, automobiles or national defense. And by 2010, health care expenditures are expected to double to $2.6 trillion—15.9 percent of our Gross Domestic Product, according to the Centers for Medicare and Medicaid Services. There are many reasons to the significant increase in cost. While addressing this challenge is a hot political, social and ethical issue, there is an agreement that healthcare information can be used to guide toward a more effective and efficient use of healthcare resources.

(B) The role of data in healthcare—analyses of adequate healthcare data can be used for a wide range of application including: identifying ways to improve the effectiveness, safety and efficiency of health care delivery; retrospective population studies to understand risk factors and therapeutic option; public health and epidemiological studies; the understanding of healthcare errors and compliance issues and the understanding of the effectiveness of healthcare innovations communication to healthcare professionals and consumers (healthcare marketing). Many of these applications contribute to a better and more efficient healthcare system.

(C) Health transaction data sources—healthcare claims data, transaction data and medical data is being created, stored and communicated by various healthcare organizations. Healthcare providers frequently initiate large amounts of data as they diagnose, perform various clinical tests, perform medical procedures, and prescribe treatment. Elements of the clinical information also exist with the laboratories, pharmacies, HMOs and other healthcare payers, as well as a range of other service organizations such as clearinghouses and PBMs. Health transaction data is protected by privacy standards such as the HIPAA in the USA. In many different areas of the healthcare system data is being used for both internal applications within the organization that generated the data or for external applications, by properly de-identifying transaction data from patient identifiers.

(D) Aggregated de-identified data, physician level—In the pharmaceutical industry data is commonly used to direct pharmaceutical companies promotional efforts. Pharmacy datasets are typically aggregated to the physician (or prescriber) level and include share and volume data (Total Rx and New Rx or TRx and NRx). In generating this datasets, the original identifiable and complete data is de-identified and aggregated and therefore a "lower resolution" of data is available as an output, or in other words a portion of the original dataset is lost and no longer available for analyses.

(E) Longitudinal patient-level data—A second-generation level of data is now also available for pharmaceutical applications. Frequently called anonymous (or de-identified) patient-level data, these datasets link several records of the same person over time, therefore providing better understanding of both consumers and physicians. These datasets never include identifiable patient information and sometimes also lack physician identifiers. In generating this datasets, the original identifiable and complete data is de-identified and aggregated and therefore a "lower resolution" of data is available as an output, or in other words a portion of the original dataset is lost and no longer available for analyses.

(F) Direct-to-consumer, DTC as a trend—Specifically the pharmaceutical industry (and sometimes the medical device manufacturers), communicate directly with consumers to drive awareness to various medical conditions and to specific products. Direct-to-Consumer marketing has grown significantly since the FDA has relaxed its regulation on such activities in 1997. DTC initiatives range from advertising initiatives to initiatives that are very well targeted through a one-to-one dialog. Some initiatives are specifically aimed at users of a particular medication to encourage them to use the product correctly, or as prescribed, and for chronic conditions, encourage users to use the medication for a long period of time (persistency). DTC promotional activities are examples of Health Programs as defined herein.

(G) Adherence to therapies (compliance) as a major health issue—many healthcare stakeholders appreciate the need to enhance compliance to medical treatments prescribed by doctors. The World Health Organization published a study under the name "Adherence to Long-Term Therapies: Evidence for Action". As part of the introduction to the study the WHO wrote—Adherence to therapies is a primary determinant of treatment success. Poor adherence attenuates optimum clinical benefits and therefore reduces the overall effectiveness of health systems. "Medicines will not work if you do not take them"—Medicines will not be effective if patients do not follow prescribed treatment, yet in developed countries only 50% of patients who suffer from chronic diseases adhere to treatment recommendations. Improving compliance is one are that substantial more progress is needed with benefits to all healthcare stakeholders. Various sophisticated Health Programs, as defined herein, are launched by various sponsors with the goal of improving compliance.

(H) Nature of health programs and data collected; type of intervention and possible combinations—There are many different types of health programs and likewise different entities who may be interested in sponsoring and delivering these programs. Goals can vary based on sponsors (government, HMOs, employers, pharmaceutical companies, etc.). Health programs can have the goals of raising product awareness, acquiring new customers, encouraging patient compliance with medication regimen, expanding the overall diagnosed market, improve healthcare outcomes, improve quality of life, reduce overall cost to the healthcare system, etc. Other non-pharmaceutical manufacturer sponsored health programs may include public health efforts or disease/care management as well as other health promotion programs promoted by healthcare associations, payers and others.

(I) In-sufficiency of target consumer program measurement while data exist because of privacy issues—The challenge of measuring the impact of a consumer health program becomes significant whenever the health program sponsor does not have the full healthcare information of the target population at their disposal. Blocked by both access to data as well as privacy challenges, sponsoring organizations have to assess the impact of their efforts with very limited methods. As described above in this section, HIPAA provides substantial limitation on Personal Health Information and existing de-identification method may render the information useless for the purpose of measuring the impact of health programs. Naturally, with limited measurement abilities, less resources are directed by sponsors to valuable health programs such as compliance programs.

(J) "Soft" measurement of health programs, activity or self-reported measurement—As a result of the above mentioned limitations, existing methods for assessing health programs and marketing programs that effect a subset of the consumer/patient population include self reported data such as patient surveys or activity measurement such as the number of messages sent to the consumer, etc. Other approaches include: (i) consumer panels where consumers are surveyed on some regular basis. (ii) regionally or otherwise focused initiatives can be measured by a regional analysis if (iii) other fairly complex and limited methods to infer patient behavior.

Now, in these and countless other (non-health system related) examples, many useful advances to understanding would occur if the data privacy restrictions were lifted—since records could be aligned according to name and/or ID—thereby presenting to researchers a portrait of reality at substantially higher resolution. However, if this merger were allowed, then countless opportunities to breach personal privacy would occur in violations of laws and regulations— eventually causing many individuals to stop providing accurate information to their HMOs and healthcare providers, the census bureau, and/or to stop using their credit card, etc. Accordingly, there is a long felt need in the art for a protocol that will allow higher resolution query and manipulation of privacy sensitive data while simultaneously allowing individual privacy to be preserved. Furthermore, it is reasonable to consider that any progress in the direction of better data utilization while maintaining privacy would constitute progress.

Key Definitions:

Data Source Entity—organizations that generate, capture or store (for example—in the health care industry) medical and claims data that includes identifiable personal health information. That includes physician office, hospitals, labs and other healthcare providers; pharmacies; and HMOs, MCOs, self-insured employers, insurance companies, PBMs and other such entities. It also includes claims clearinghouses and any other "Covered Entities" as defined under HIPAA. Conceptually, the source-entity also includes other entities operating as a vendor for the source-entity under a privacy agreement (such as HIPAA Business Associate Agreement). Furthermore, there are non-health care data source entities—such as credit card companies, credit bureaus, insurance companies, banks, the census bureau, social service agencies, law enforcement agencies, and the likes, all of which share common functionality as collectors and maintainers of myriads of data including therein personal identifiable data.

Data Consumer Entity—organizations that would like to get analytics services to answer marketing, operational, quality, (for example) health outcome or other business related question regarding a specific (for example) health program, initiative, a subset or all of the marketplace, etc. Data Consumer Entities are interested in strategic and tactical analyses to help them optimize their resource investment to achieve their objectives. Examples can be the government, researchers, product and service (for example) healthcare companies, etc. Specifically in healthcare, detailed population information can have a remarkable role in the identification of public health trends, retrospective health outcomes, clinical research and development, medical errors and other valuable healthcare applications.

Crossix—an expression that includes the instant protocol according to any of its embodiments—and derivative uses thereof (see FIGS. 4 & 5 for preferred embodiment details)

Health Program—a program (used as specific example for the preferred embodiment of the instant invention) that affects a subset of the overall potential population. Typically patients, consumers or healthcare professionals will opt-in to participate in such a program and if the organization sponsoring it is not covered by HIPAA, the sponsoring organization will adhere to its published privacy policy. Typically Health Programs capture personal identifying information. Health Programs may include for example compliance programs or may include a broadcast advertising component (such as TV commercials) encouraging consumers to call a toll-free number or go to a web-site for further information. Frequently, at the call center or web-site, some consumer information is captured.

Typical Identifiable Data Captured in a Health Program—Some combination of the following fields or similar to those: First Name; Last Name; Date of Birth Or Year of Birth; Zip Code; Full Address; Phone Number(s); Fax Number(s); E-Mail; Prescribing Doctor Name, Address or Other Identifiers; Medical Condition or Drug Prescribed; Gender; Social Security. NOTE: Variability of data discussion—personal data frequently changes. (See discussion on this in U.S. Pat. No. 6,397,224 and 'Math, Myth & Magic of Name Search & Matching' by SearchSoftwareAmerica) A subset of this data jointly can serve as an identifier with high probability of uniqueness. For example, Date of Birth and phone number could serve jointly as unique identifiers. Data Source Entity information structure (of typical health care related identifiers) may include all or some of the above plus a unique member ID. (Note: See U.S. Pat. No. 5,544,044; U.S. Pat. No. 5,835,897 and U.S. Pat. No. 6,370,511 for detailed description of healthcare data structure.)

ADVANTAGES, OBJECTS AND BENEFITS OF THE INVENTION

Ergonomic Issues: Preferred embodiments of the instant invention allow analysis of "source-entity" raw data at is original, most detailed form (high resolution data) including full access to all of the privacy sensitive data currently at its disposal while simultaneously maintaining existing privacy restrictions to the aggregator processor. In addition, high-resolution analysis may be performed at multiple different "source-entities" each of which preserves its privacy restrictions, yet under certain conditions the data can be aggregated by the aggregator processor to provide a more comprehensive analysis.

Economic Issues: Preferred embodiments of the instant invention allow exploitation of an order of magnitude more value potential from the data currently resident at the "source-entity" processors while only adding nominal expenses at the "aggregator" processor. Furthermore, expenses at the "aggregator" processor are essential to define and provide new avenues of access to the ensemble of privacy sensitive data located at the "source-entity" processors.

Technical Issues: Preferred embodiments of the instant invention essentially are composed of software packages that each respectively sit in different data processing machines where they interact with database packages on that respective machine or a machine connected to it via a network. The software packages are interconnected with each other using standard data-communications facilities (e.g. Internet, VPN, etc.). Accordingly, from a technical perspective, embodiments of the instant invention are convolutions of quasi-familiar software modules—allowing implementation to be straightforward in today's data complexity environment.

SUMMARY OF THE INVENTION

The aforesaid longstanding needs are significantly addressed by embodiments, of the present invention, which specifically relates to The Privacy Preserving Data-Mining Protocol. The instant protocol is especially useful in society-computer interactions wherein there exist actual needs or economic benefits from allowing higher resolution query and manipulation of privacy sensitive data while simultaneously not allowing individual privacy to be breached.

Embodiments of the instant invention relate to a Privacy Preserving Data-Mining Protocol, (see FIG. 3) operating between a secure "aggregator" data processor 300 and at least one secure "source-entity" data processors 350, wherein the "aggregator" and the "source-entity" processors are interconnected via an electronic data-communications topology 399, and the protocol includes the steps of:

(A) on the side of the "aggregator" processor:

(i) from a user interface—accepting 315 a query against a plurality of the predetermined attributes and therewith forming a parameter list, (ii) via the topology—transmitting 320 the parameter list to each of the "source-entity" processors, (iii) via the topology—receiving 325 a respective file from each of the "source-entity" processors, (iv) aggregating 330 the plurality of files into a data-warehouse, (v) using the parameter list, extracting 335 query relevant data from the data-warehouse, (vi) agglomerating 340 the extract, and (vii) to a user interface—reporting 345 the agglomerated extract; and (B) on the side of each processor of the at least one "source-entity" processors:

(i) accumulating 355 data-items wherein some of the data-items have privacy sensitive micro-data, (ii) organizing 360 the data-items using the plurality of predetermined attributes, (iii) via the topology—receiving 365 a parameter list from the "aggregator" processor, (iv) forming 370 a file by "crunching together" the data-items according to the parameter list, (v) filtering out 375 portions of the file which characterize details particular to less than a predetermined quantity of micro-data-specific data-items, and (vii) via the topology—transmitting 380 the file to the "aggregator" processor.

After turning to FIGS. 4, 4A (a conceptually more detailed version of FIG. 4), and 5, lets examine each of the sub-step and explain what it accomplishes and how collectively it results in accomplishing an improvement over the aforesaid long felt need.

Embodiments of the Privacy Preserving Data-Mining Protocol are operating between a secure "aggregator" data processor—which is a central data processing machine—and at least one secure "source-entity" data processors—which are other data processing machines that respectively include records having privacy identified data such as name, identity number, or the likes. Until the present invention, it was the practice of the "source-entity" machines to query these records for internal use using the privacy identified fields—such as looking as an individual person's records as a single unit, etc. However, it is generally legally prohibited for the "source-entity" to share and/or sell data having the privacy sensitive fields or fields that would allow correlation with other data whereby the privacy sensitive identifier could be "guessed". Therefore, it has become common practice for "source-entity" data gatherers to condense their data around larger cluster variables—such as by age group or by state or by gender. While this practice preserves the privacy of individuals by dissolving their identity into an ensemble of others, it simultaneously precludes external researchers from benefiting from the richness of the "source-entity" data.

Now, the "aggregator" and the "source-entity" processors are interconnected via an electronic data-communications topology—such as the Internet, or a virtual private circuit or the likes; all of which eliminates any need for the processors to be collectively centralized. Rather, the processors may remain distributed, as is the case in today's world.

To summarize up to here, the protocol operates using data-communications facilities to interconnect a central aggregator processor with at least one source-entity processors. The source entity processors each have respective privacy sensitive data content along with other data content aspects.

Now, according to the instant protocol, on the side of the "aggregator" processor (A) there are seven sub-steps. First, a sub-step of "(A-i) from a user interface—accepting a query against a plurality of the predetermined attributes and therewith forming a parameter list" that establishes the aggregator as the focus of a query that may include problematic privacy-sensitive information that the source-entity cannot release to an "outsider". Intrinsically, in the context of the instant invention, the parameters of the list may include identity disclosing specifics—which probably do not pass ordinary criteria of even nominal privacy thresholds, and/or broader variables—which probably do pass ordinary criteria of normal, rigid, or strict privacy thresholds.

These identity-disclosing specifics may be such things as name, personal identity number or simple data combinations that would allow breach of privacy if applies to disclose identity. What is important in the further application of the instant method is that these identity-disclosing specifics are part of a large enough list in the processing of a query so that the query result will present sufficient statistical distribution to protect the "reverse engineering" of the result back to any individual in the initial query list. For example, the instant method can ask about the status of Tom, Dick, Harry, and a further collection of individuals—and obtain results from that query—so long as the statistical character of those results will not allow correlation of a result specific back to an individual. Thus it may be that the query includes a list of 10,000 personal IDs and the results show that these individuals belong to group A with 60% probability, Group B with 25% probability, and one of Groups C-E with the remaining 15% probability. Accordingly, transmitting the parameter list may include transmitting a sufficiently large list of identity disclosing specifics.

Simply stated, the aggregator may accept a query that includes lots of identity specifics (e.g. a list of names or a combination of a few fields that together can allow identification)—the type of query that one does not expect to be answerable in any privacy preserving fashion. This sub-step essentially converts a model base postulate about the data (that relationships that the user wonders) into a formal language query phrases according to shared variable definitions mutually accepted by the aggregator and the source-entities. The parameter list would include a definition of the population to be analyzed such as by geography, age or other attributes. One of the most novel features of the instant protocol is that the parameter list may even include specific individuals by name or ID or the likes. It will simply be necessary that the number of the individuals in any population definition be large enough to dilute any definitive conclusion about an individual's personal data into the "sea" of the group (of names') data. According to some specific instant embodiments, all or part of the parameter list is encrypted.

Next, the sub-step of "(A-ii) via the topology—transmitting the parameter list to each of the "source-entity" processors" sends the formalized query—in whatever format is mutual agreed to by the aggregator with each respective source-entity. It may occur that the aggregator phrases the formal query differently to some source-entities than to other source-entities—and this is probably the most pragmatic embodiment. Sometime thereafter is the sub-step of "(A-iii) via the topology—receiving a respective file from each of the "source-entity" processors" whereby the aggregator receives some answer (or a null answer) from each source-entity; however (as we will understand from the source-entity side of the instant protocol) while the question included parameters which request that the source-entity correlate data according to privacy sensitive data aspects, the answer is condensed into an identity free representation.

For example, in the testing of an unusual postulate, the query asks to characterize patients who have a specific health problem and who receive a specific therapy in terms of the seniority of their attending physicians. In order to answer the query, the source entity must compare records with same patient names & IDs to name & ID specific physician records. However, the answer is a table of seniority brackets of physicians compared to a data cluster of multiple patients' data. According to this type of example, a pharmaceutical company user could find out from a plurality of HMOs source-entity records if the company should market its therapy primarily to senior physicians or primarily to junior physicians, or both. Simply stated, the query test one possible postulate about the humanity of physicians—and that query has interesting economic implications for pharmaceutical companies.

Next, the sub-step "(A-iv) aggregating the plurality of files into a data-warehouse" goes further to protect privacy by bundling the responses of the individual source-entities into a large source-entity de-identified data collection and at the same time deliver results from multiple distributed and different data-sources. Thus, the sub-step "(A-v) using the parameter list, extracting query relevant data from the data-warehouse" allows for getting all the relevant data of the data warehouse to a single temporary collections including responses from one or more source-entity query-response cycles and other data which may come from the ordinary reporting of source-entities or others. Now, in sub-step "(A-vi) agglomerating the extract", a condensed picture of all of the data which may uphold or reject the postulates of the query are summarized together; and finally in sub-step "(A-vii) to a user interface—reporting the agglomerated extract".

Furthermore, (B) on the side of each processor of the at least one "source-entity" processors, the first two sub-steps call for ordinary operations—such as "(B-i) accumulating data-items wherein some of the data-items have privacy sensitive micro-data, and (B-ii) organizing the data-items using the plurality of predetermined attributes". Thereafter, the sub-steps (B-iii) via the topology—receiving a parameter list from the "aggregator" processor" let the source-entity begin to participate in the user initiated "project" that is being managed by the aggregator.

From here, the next sub-step "(B-iv) forming a file by "crunching together" the data-items according to the parameter list" causes each respective source-entity to perform the necessary internal data base queries and to perform the necessary correlations and formation of temporary data-interrelationships in order to know the local answer to all or part of the initial user query that was sent through the aggregator. If the parameter list included specific individuals by name or ID or the likes, "Crunching together" may involve name matching through "fuzzy logic" and other name matching algorithms of the population defined by the parameter list with the source-entity database names, in addition to the other steps defined above. Having done that, the sub-step "(B-v) filtering out portions of the file which characterize details particular to less than a predetermined quantity of micro-data-specific data-items" eliminates portions of the answer which might allow the user to guess the identity some data attribute—because that data attribute belongs to an individual or to a very small group of members. This step is necessary—since it eliminates one degree of trust from the relationship between the source-entity and the aggregator. In all good conscience, the source-entity has preserved his duty to protect the identity of individuals in his data collection. Simply stated, in the context of the instant invention, filtering is synonymous for implementing a privacy threshold at the "source-entity" level. Finally, to complete the protocol, there remains the sub-step of (B-vi) via the topology—transmitting the file to the "aggregator" processor" is accomplished according to well-known methods in the art.

Reviewing the relationships between the user, the aggregator, and the source-entities, one notices that the user is permitted to phrase queries that may cause a source-entity to perform database functions requiring identity specific data—but this does not cause the identity, per se, to be revealed outside of the source-entity jurisdiction. Secondly, the aggregator may now collect and assemble identity protected reports from numerous data collections (source-entities) and assemble them into a single report—thereby potentially greatly increasing the statistical significance of conclusions that can be drawn from the aggregator report to the user. Furthermore, the very revealing aspect that all or most of the result may be coming from a single source-entity is protected. For example, it might be very politically sensitive to realize that attitudes of physicians in one HMO radically differ from physicians in all other HMOs—and this peculiarity is hidden from the user by using an aggregator.

According to a first preferred embodiment of the instant invention, agglomerating the extract includes filtering out portions of the extract which characterize details particular to less than a predetermined quantity data-items. According to the preferred variation of this embodiment filtering out portions of the extract which characterize details particular to less than a predetermined quantity data-items includes the predetermined quantity being selected from the list, ordinal number, percentage of instances in the data-warehouse, data instances outside of mean plus predetermined number of standard distribution units.

According to a second preferred embodiment of the instant invention, agglomerating the extract includes filtering out portions of the extract so that only identity-free micro-data or identity-free aggregated data remains.

According to a third preferred embodiment of the instant invention, accepting a query includes performing a preprocessing privacy check against a predetermined source-entity data-ensemble model.

According to a fourth preferred embodiment of the instant invention, "crunching together" the data-items includes joining data-items having a mutual or similar micro-data-specific (for example similar names with variations such as nick name, prefix, suffix, etc.).

According to a fifth preferred embodiment of the instant invention, selected from the list of sub-steps aggregating, extracting, agglomerating, accumulating, organizing, and crunching, at least one sub-step includes fuzzy matching.

According to a sixth preferred embodiment of the instant invention, (on the source-entity processor side) filtering out portions of the file which characterize details particular to less than a predetermined quantity of micro-data-specific data-items includes selecting the predetermined quantity from the list, an ordinal number, a percentage of instances in the data-warehouse, data instances outside of statistical mean-or-median plus-and/or-minus a predetermined number of standard deviation units.

According to a seventh preferred embodiment of the instant invention, accepting a query includes transforming the query into a standardized query—capable of resulting in a syndicated reporting of the agglomerated extract. In this context, it is preferred that, a Markup Language be used which directly links aspects of the query with aspects of the reporting—since it is anticipated that various industries will adopt the instant protocol to produce substantially real-time "testimonies".

Some collateral embodiments of the instant invention relate to (see FIG. 6) a program storage device 600 readable by machine, tangibly embodying a program of instructions executable by the machine to perform method steps for "aggregator" data processor functions in a Privacy Preserving Data-Mining Protocol, said method steps including: (i) from a user interface—accepting 610 a query against a plurality of the predetermined attributes and therewith forming 620 a parameter list, (ii) via an electronic data-communications topology—transmitting 630 the parameter list to at least one "source-entity" processors, (iii) via the topology—receiving 640 a respective file from each of the "source-entity" processors, (iv) aggregating 650 the plurality of files into a data-warehouse, (v) using the parameter list, extracting 660 query relevant data from the data-warehouse, (vi) agglomerating 670 the extract, and (vii) to a user interface—reporting 680 the agglomerated extract.

Other collateral embodiments of the instant invention relate to (see FIG. 7) a program storage device 700 readable by machine, tangibly embodying a program of instructions executable by the machine to perform method steps for secure "source-entity" data processor functions in a Privacy Preserving Data-Mining Protocol, said method steps including: (i) accumulating 710 data-items wherein some of the data-items have privacy sensitive micro-data, (ii) organizing 720 the data-items using the plurality of predetermined attributes, (iii) via an electronic data-communications topology—receiving 730 a parameter list from an "aggregator" processor, (iv) forming 740 a file by "crunching together" the data-items according to the parameter list, (v) filtering 750 out portions of the file which characterize details particular to less than a predetermined quantity of micro-data-specific data-items, and (vi) via the topology—transmitting 760 the file to the "aggregator" processor.

Notwithstanding the aforesaid, general embodiments of the instant invention (see FIG. 8) relate to a Privacy Preserving Data-Mining Protocol 800, substantially as herein before described and illustrated, firstly characterized by having at least one of mutually independent secure "source-entity" data processors 810 respectively forming 820 a file by "crunching together" data-items according to a parameter list, and thereafter respectively filtering 830 out portions of the file which characterize details particular to less than a predetermined quantity of micro-data-specific data-items; and secondly characterized by having a secure "aggregator" data processor 850 aggregating 860 the plurality of files into a data-warehouse. Furthermore, other variation embodiments of the instant protocol are bi-directional—meaning that the fundamental relationship between the "source-entity" and "aggregator" processors is reversed and/or reversible!

Thus, it is accurate to summarize that the fundamental embodiments of the Privacy Preserving Data-Mining Protocol of the instant invention operate between a secure "aggregator" data processor and at least one secure "source-entity" data processors. The "aggregator" and the "source-entity" processors are interconnected via an electronic data-communications topology. The protocol is characterized by including the data-communications coordinated steps of: the at least one mutually independent secure "source-entity" data processors respectively forming a file by "crunching together" data-items according to a parameter list, and thereafter respectively filtering out portions of the file which characterize details particular to less than a predetermined quantity of micro-data-specific data-items; and the secure "aggregator" data processor aggregating the plurality of files into a data-warehouse.

Embodiments of the protocol of the instant invention are applicable to many arms-length data rights relationships, including (for example) those that exist between healthcare providers, pharmacies, PBMs or Health Maintenance Organizations (HMOs) & Pharmaceutical-Companies; electronic commerce & market research; banking & insurance; census bureau & other government agencies; auditors & independent procurement/service organizations; and the likes.

A further class of embodiments of the Privacy Preserving Data-Mining Protocol of the present invention is worthy of note; and these are interim data merger enabled embodiments. Simply stated, these embodiments allow for the linkage of data items as related to a common entity. For example, an individual was a regular member of a first health care medical expense insurance plan and then switched to become a member of a second health care medical expense insurance plan. If the data sources are careful to encrypt the identifying portions of each record using a common encryption "key", then further down the data processing circuit it will be possible to link records related to a common individual without compromising the identity of that individual. Of course, special care must be taken that the entity performing the linkage is not capable of knowing the key and decryption function; because knowing these facets would enable a breach of the individual's privacy. (Note: U.S. Pat. No. 6,397,224 considered some aspects of using third party key holding to respect individual privacy—albeit without facilitating anonymous linkages between a plurality of data records.)

Returning now to FIGS. 3 and 8 (and Mutatis Mutandis to their respective program storage devices), it can now be appreciated that there are numerous locations where an encryption of individual identification and/or merger of data for individuals could be facilitated. By way of non-limiting example, on the "aggregator" processor side, the encryption and/or merger could be enable during the sub-steps: receiving a respective file, or aggregating the plurality of files; or on the "source-entity" processors' side, the encryption and/or merger could be enabled during the sub-steps: organizing the data-items, forming a file, or filtering out portions of the file.

Thus there are at least two different situations where data from the data source is returned already aggregated, after analysis as well as a second option where data is release at the micro-level (each person's data), but the person identity information, for the matched population, is replaced with a unique encryption key, such as a one way hash or Advanced Encryption Standard (AES) or the likes. This compatible encryption for the identifying micro-level data preserves the ability to know that the two records belong to the same identity, but preserve the privacy of the identity of that person. Each situation has viable options, albeit with respectively different advantages and disadvantages.

According to the preferred variation of this interim data merger enabled class of embodiments, the ability to link micro-level records related to the same identity at the data aggregator level is preserved—even if the records came from two different data sources.

Recall, at substantially each data source there is preformed a name matching to identify all of the records for a certain identity (e.g. for Jane Doe). In that identity matching, the result may be several combinations of personal identifiers for the same person—for example (Jane Doe, (Boston, Mass.), health-plan ID 1234) and (Jane Doe, (New York, N.Y.) health-plan ID 5678) may both appear in a single data source. Since the name matching preferably has "fuzzy logic", the software in the data source will find both. When releasing data from the data source to the data aggregator, the personal IDs will be encrypted—but using the same key in all data sources—a key that will preferably not be known to the Crossix protocol operator, but only a trusted third party such as an escrow agent. Now assume that a second data source also had data for (Jane Doe, (New York, N.Y.) health-plan ID 5678).

Now, at the data aggregator, data will be received from each data source, and the desire is to know that one instantiation with variation of Jane Doe is the same as another for a second data source. The way to achieve that is to encrypt more than a single ID for each person—so in the data released from the first data source—we will get both keys and the healthcare data (WXYZ (key1), ABCD (key2), other de-identified healthcare data) and from the second data source we will get (WXYZ, other de-identified healthcare data). Because of the fact that we encrypt several key that can uniquely identify the person, we can link their healthcare record for a more complete analysis. For example, if a person filled a prescription in one pharmacy, took a job with another employer (and therefore received a new health plan ID) but still used the same pharmacy, and eventually moved to another city; then, using the current merger embodiment, one could analyze whether that person is compliant and persistent in refilling the prescription for his medication (an important healthcare datum for that person)—even though the identity of that person is not knowable to the analyzer.

Thus, it should be apparent to the ordinary man of the art that the afore-mentioned interim data merger enabled embodiments and the likes are essentially elaborations of various imbedded encryption strategies for micro-data and their respective potential advantages—all in the context of the instant Privacy Preserving Data-Mining Protocol.

Notices

The present invention is herein described with a certain degree of particularity, however those versed in the art will readily appreciate that various modifications and alterations may be carried out without departing from either the spirit or scope, as hereinafter claimed.

For example, every step requiring a transmitting of data (or of at least one file) and every respective associated step requiring receiving of that data (or of that at least one file) may preferably include respective encryption and decryption—however the nature and quality of this security aspect is well understood by the systems administrator; in the context of his specific regulatory environment, etc. Nevertheless, it is generally preferable to include some degree of data transmission security. (Compliant with this rationale, process occurring in processors of running the instant protocol should be secure—and certified as such.)

Another example relates to applications of the instant protocol, in that it is anticipated that countless examples of privacy preservation may be achieved between heretofore strictly separated entities ("a query relationship")—such as pharmaceutical companies and HMOs (Health Maintenance Organizations), market researchers and credit card companies, government agencies and the census bureau, Law Enforcement Agencies seeking to understand general aspects of a social problem (as recorded in countless private databanks) without needing a search warrant for any specific individual or class or individuals, and similar heretofore detail-opaque query and answer data opportunities. Thus, it is anticipated that at least one of an at least two electronic data providers is selected from the list: data source entity, data consumer entity, health program, pharmaceutical manufacturer/distributor, public health regulator/monitor; credit card bureau, market research organization, banking consortium, census bureau, government agency, or the likes.

A further example, relates to the inclusion of at least a predetermined minimum number of individuals (identified by name or ID, address, phone number, date of birth, e-mail or the likes or a combination thereof) into a "parameter list" (that is formed or transmitted in the instant protocol)—and these individuals may be persons or legal entities or individual motor vehicles or individual computers or serial numbering industrial products or legal registration numbers or license numbers or the likes. Returning to the abovementioned aspects of preferable encryption, it is certainly strongly advised that regardless of the general level of encryption elected, a parameter list including "individuals" should carry a stronger level of encryption. Nevertheless, in each "query relationship" there are different legal standards which may be applicable—such as in health care in the USA, interim between-party results must be HIPAA (Health Insurance Portability and Accountability Act of 1996) de-identified without micro-data specific content or substantially equivalently provably statistically intractable.

Thus, in describing the present invention, explanations are presented in light of currently accepted Data-Processing theories and Legal-Privacy models. Such theories and models are subject to quantitative (computational) & qualitative (cultural) changes, both adiabatic and radical. Often these changes occur because representations for fundamental component elements are innovated, because new transformations between these elements are conceived, or because new interpretations arise for these elements or for their transformations. Therefore, it is important to note that the present invention relates to specific technological actualization in embodiments. Accordingly, theory or model dependent explanations herein, related to these embodiments, are presented for the purpose of teaching, the current man of the art or the current team of the art, how these embodiments may be substantially realized in practice. Alternative or equivalent explanations for these embodiments may neither deny nor alter their realization.

BRIEF DESCRIPTION OF THE DRAWINGS

In order to understand the invention and to see how it may be carried out in practice, embodiments including the preferred embodiment will now be described, by way of non-limiting example only, with reference to the accompanying drawings. Furthermore, a more complete understanding of the present invention and the advantages thereof may be acquired by referring to the following description in consideration of the accompanying drawings, in which like reference numbers indicate like features and wherein.

DETAILED DESCRIPTION OF THE INVENTION

Figure 1:
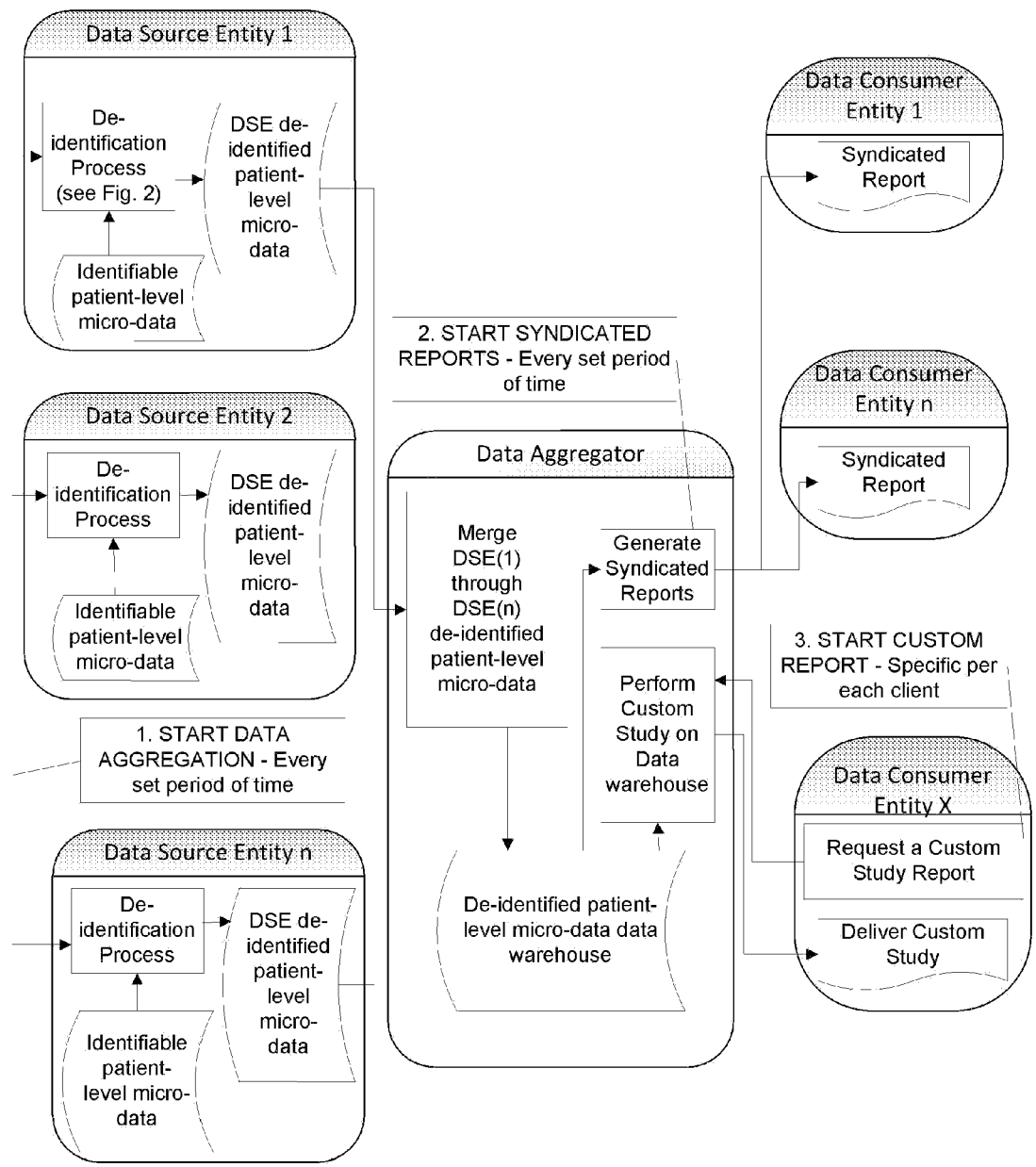
FIGS. 1 & 2 illustrate schematic flow charts of prior art methods.

Note: Solely for the sake of simplicity—in order that the ordinary man of the art may appreciate the unique facility of the instant protocol, the (non-limiting) example of detail will be for the health care industry. One reason for this choice is that compliance with HIPAA (Health Insurance Portability and Accountability Act of 1996) is a well-known semi-intractable problem that is adequately documented for use as an objective metric of the usefulness of the instant invention. Thus, the instant example relates to using embodiments of the Protocol of the present invention as a computer-implemented method for profiling health programs while maintaining participant privacy. (The specific background details related to health care information systems are presented in the latter part of the background section.)

Simply stated, embodiments of the instant profile are computer-implemented for profiling health programs—to assist program planners such as marketing managers from pharmaceutical manufacturers or other health promotion managers to assess the aggregate behavior of a large group of participants impacted by a specific health program compared to a control group. The assessment of the impact of a particular program is done by profiling participants aggregate objective health transaction data (pharmacy, treatment, diagnosis, lab, etc.) to conclude various effects of the health program compared with a possibly defined control group while adhering to current and evolving privacy standards and laws such as HIPAA.

Objective health transaction data resides within healthcare organizations such as health service providers (doctors, hospitals, labs, etc.) and health plans (managed care plans, HMOs, PPOs, insurance companies, pharmacy benefit managers, self-insured employers, state and federal government health benefit programs, etc.). These organizations are governed by a set of privacy standards, rules and regulations such as HIPAA and therefore has severe limitation in their use of healthcare information that includes identifiable personal health information.

Here is an example to use of this instant protocol: (Background:) A pharmaceutical company that manufacture a pharmaceutical product for the treatment of multiple sclerosis has established several health programs to encourage consumers of that product to use the product persistently and correctly. Such health programs include a Call Center Program staffed by nurses who can answer ongoing questions and train consumers on how to use the product correctly and a Web-Site Program that includes health management tools and access to relevant disease information. These pharmaceutical health programs are promoted to consumers of that product who then opt-in to participate in the program. The participants of each program allow, among other things, the pharmaceutical manufacturer to analyze their data in aggregate. Some of the participants of the manufacturer health programs belong to various healthcare organizations that aggregate health transactions generated by the consumers in their ongoing consumption of healthcare services and products. This health transactions data includes diagnosis data, treatment data, pharmacy data and sometimes clinical data such as lab data and other health data.

Applying the method of the instant protocol include necessary, sufficient, and elective operations—according to the "reality" of the current non-limiting example; and these operations include: Extracting the lists of participants in the Call Center Program and the Web-Site Program (names, addresses and other possible identifiable information); Providing a definition of control group. For example, all consumers who consume the manufacturer product but are not participants in either the Call Center Program or Web-Site Program; then Providing a definition of analysis required. For example, a mathematical definition for persistent usage of the pharmaceutical product, or total cost of healthcare consumed, or hospitalization cost, etc. Some analyses can be fairly complex and use other processes and patented methods such as ETG (e.g. U.S. Pat. Nos. 5,835,897 and 6,370,511B1); (Optional) Encrypting the lists using any industry grade encryption method; and Delivering the lists of participants together to a query engine with a capability to decrypt the lists at the time of processing (optional) to one or more healthcare organizations that store health transactions. Health plans tend to be mutually exclusive, meaning if a member belongs to any plan, that member typically belongs to that one plan only or is likely to consume similar service at a similar time from only one health plan. Therefore, this algorithm can be used—by repeating the same process with multiple health plans; and then simply summing the results from all health plans.

For each health plan: The query engine runs a "fuzzy matching" algorithm to match participants in the pharmaceutical health program with the health transactions at the healthcare organization; For all the matched users the query engine runs the analysis of their health transaction data to determine the result of the requested analysis (such as persistency of using the pharmaceutical product); The query engine runs the control group analysis for all users that were not matched but meet the control group definition (for example, users of the pharmaceutical product); and Aggregate the results to the following groups: Call Center Program participants only; Web-Site Program participants only; participants in both the Call Center Program and the Web-Site Program; Control group (for example, all consumers of the pharmaceutical product that are neither participants of the Call Center Program nor the Web-Site Program).

For each group provide the following result: Name of group, % participants matched with the healthcare organization health transaction data, and statistical result of all matched members (such as average persistency rate); The query engine determines whether the number of participants in each program and the % participants matched are above a level that ensures consumer individual privacy (based on a statistical definition). If not, the query engine responds with: group name "cannot be analyzed because of privacy safeguards. Please try to define a bigger group of users"; and The query engine output for each health plan is aggregated to provide an overall output that may be shared with the pharmaceutical manufacturer.

This instant protocol method offers valuable aggregate assessment of health programs based on objective health transaction data without disclosing identifiable personal health information. Most methods used today are based on "soft measurements" of value, such as activity-based measurements (people enrolled, number of interactions, etc.) and/or self-reported data (participants fill surveys or other questionnaire regarding their behavior). Objective measurement based on health transaction could become the gold-standard to measure such activities.

Most existing analytics services in healthcare are based on a model where patient-level health transactions are de-identified and then aggregated and processed for analysis. Clearly through this process, high-resolution raw data that includes the maximum amount of information is reduced to a lower resolution data to preserve privacy and possibly other interests. Many companies, including IMS Health, Verispan (a joint venture between Quintiles and McKesson), Pharmetrics, Dendrite and others employee this model. This existing health analytics model may provide either physician level behavior or de-identified patient-level behavior and possibly a combination of both. However, while this model is very effective in analyzing longitudinal patient behavior and, in some cases, matching it to a known prescriber (such as physician), no linkage can be made to a consumer health program that only impact a subset of the market (unless the program correlate well with a limited region or cover a known group of physicians). One cannot query or analyze parameters that are no longer in the lower resolution dataset. Therefore, the existing healthcare analytics model does not provide the capability to aggregate the behavior of a group of patients by a predefined list of consumers participating in a health program.

This is only one example of the limitations of the existing healthcare analytics model that is addressed by the instant protocol.

For the above described application of the instant protocol to be properly effective, access is needed to a combined health transaction data that is: (A) large enough to provide sufficient level of matching to address privacy concerns and to enable statistically significant analysis; and (B) to represent an approximation to the distribution of the general market as much as possible (regions, demographics, type of populations and type of insurances) or allow statistical correction based on pre known parameters. For example, if the data source, a specific health plan, includes 15M lives well distributed across the country and representative in every other aspect except that this particular health plan has a formulary that prefers particular pharmaceutical products over others, a statistical analysis could be used to "correct" that preference based on national analysis of formularies.

Recalling the health care related information system background factors of the background section, substantially, the instant protocol embodiment (the Crossix Method) is a method to enable the statistical measurement of one or more Health Programs and the compounded effect of combination of multiple Health Programs based on analysis of health transaction data while complying with Data Source Entity privacy regulations and Data Consumer Entity privacy policy.

Figure 2:
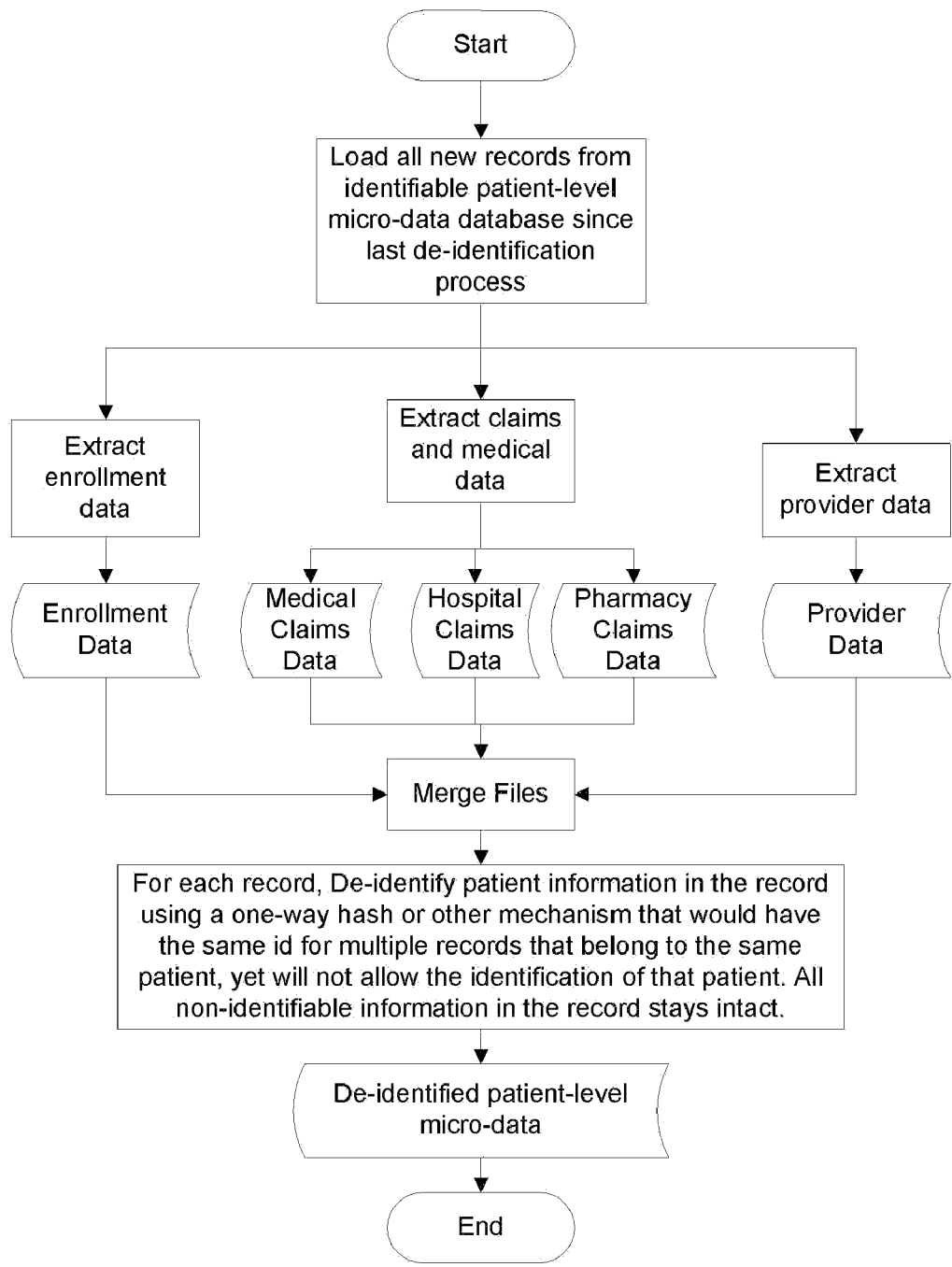
Figure 3:
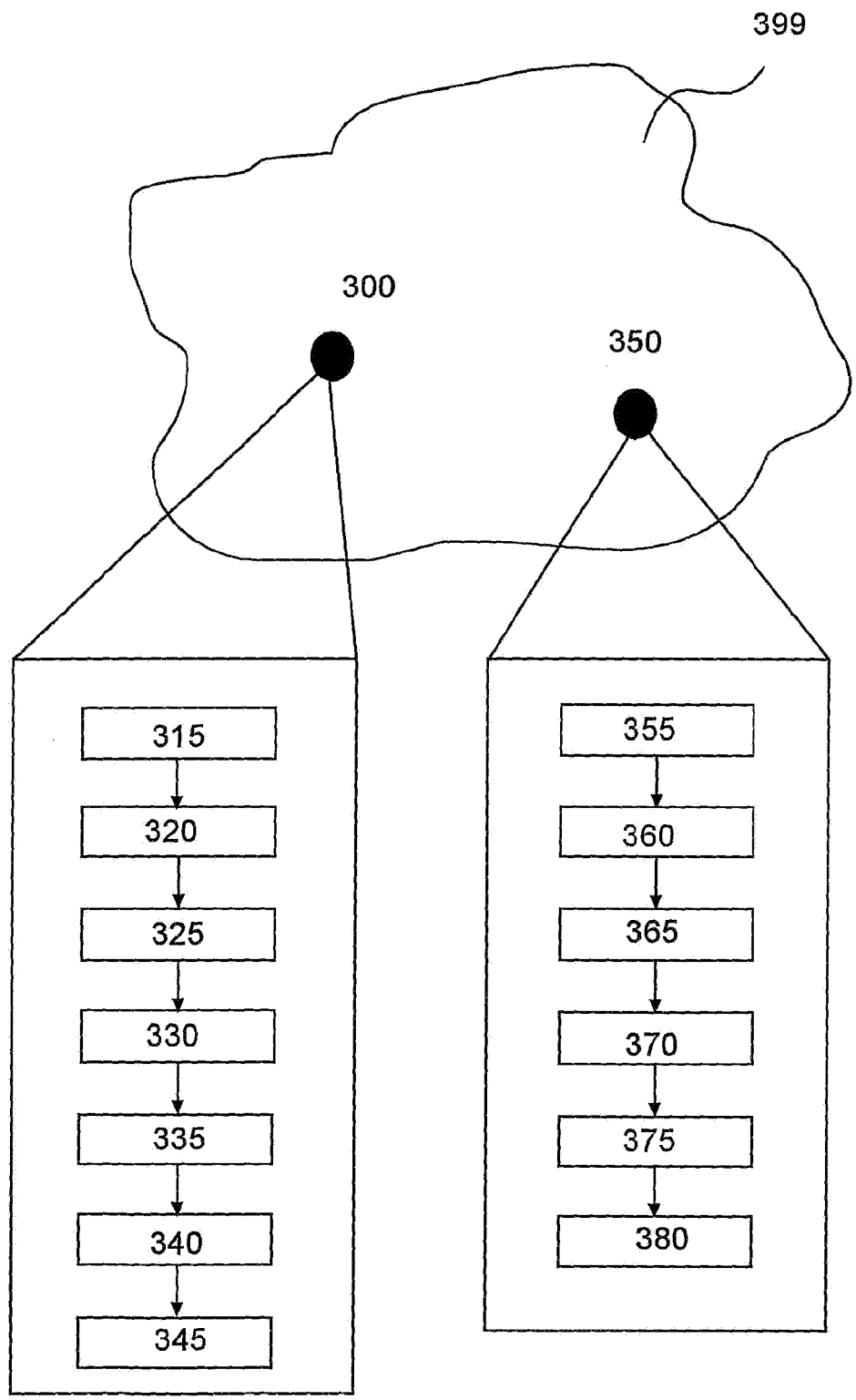
FIGS. 3 & 8 illustrate schematic views of respective embodiments of the instant protocol.
Figure 4:
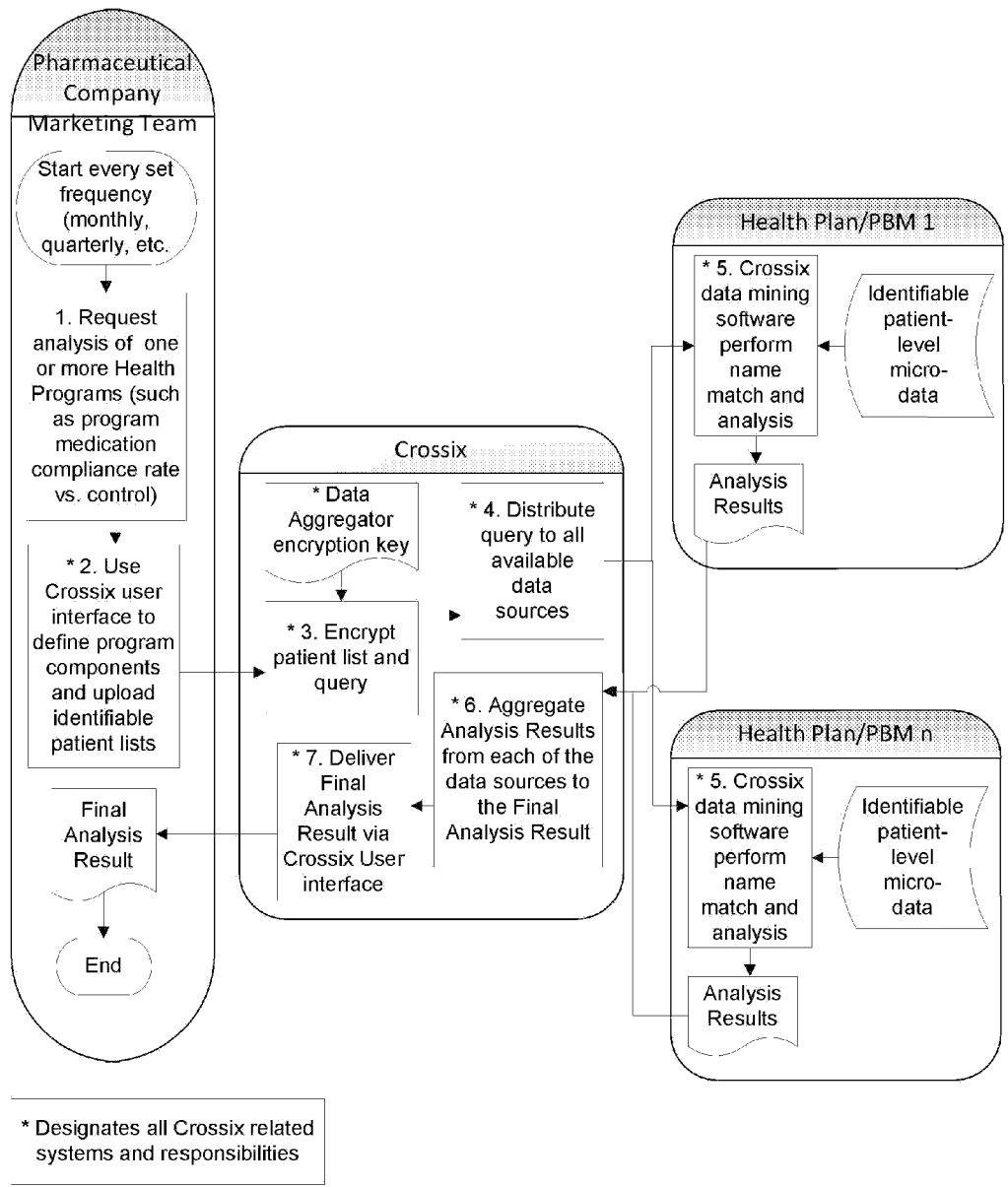
FIGS. 4, 4A & 5 illustrate detailed aspects of the preferred embodiment of the instant protocol.
Figure 4A:
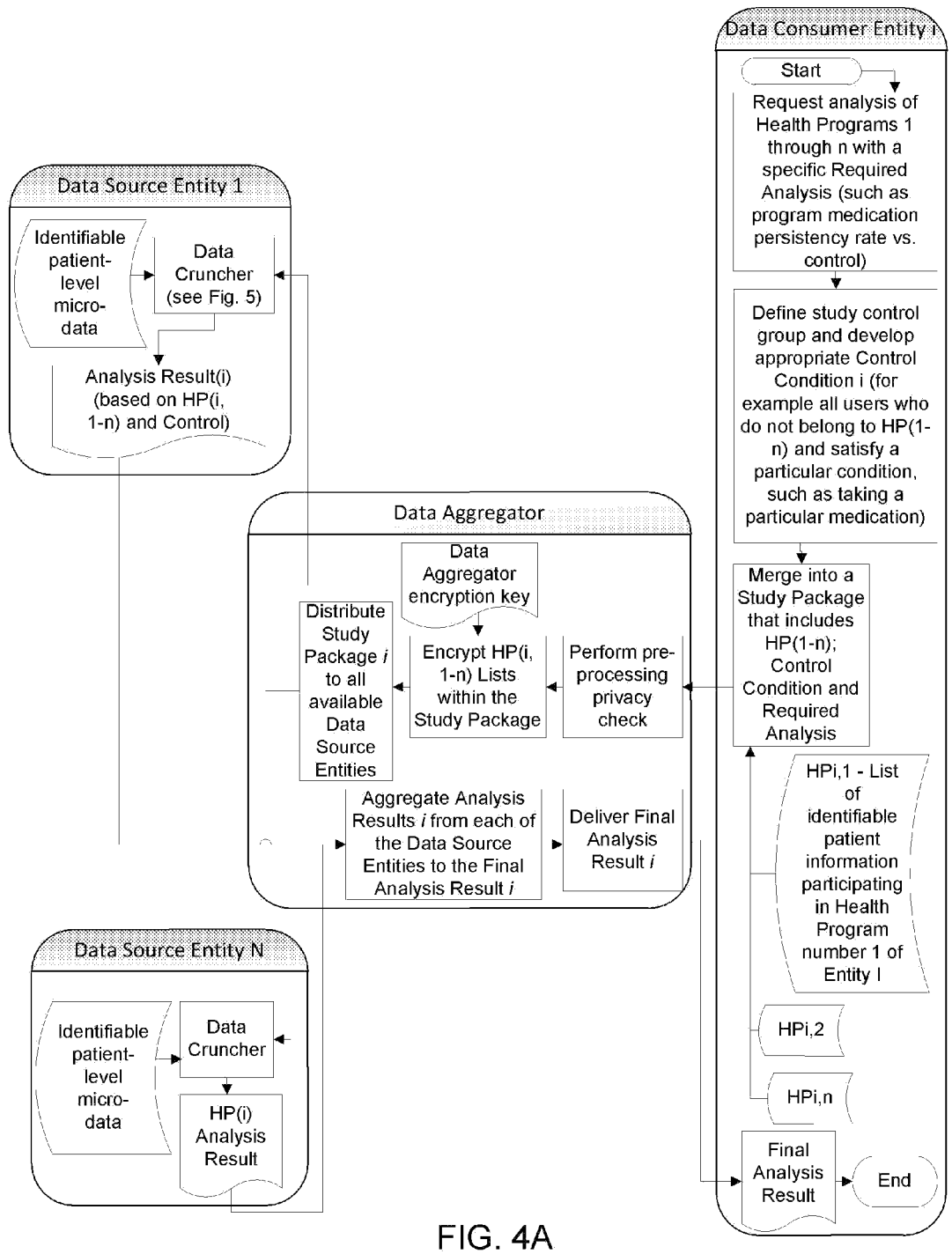
Figure 5:
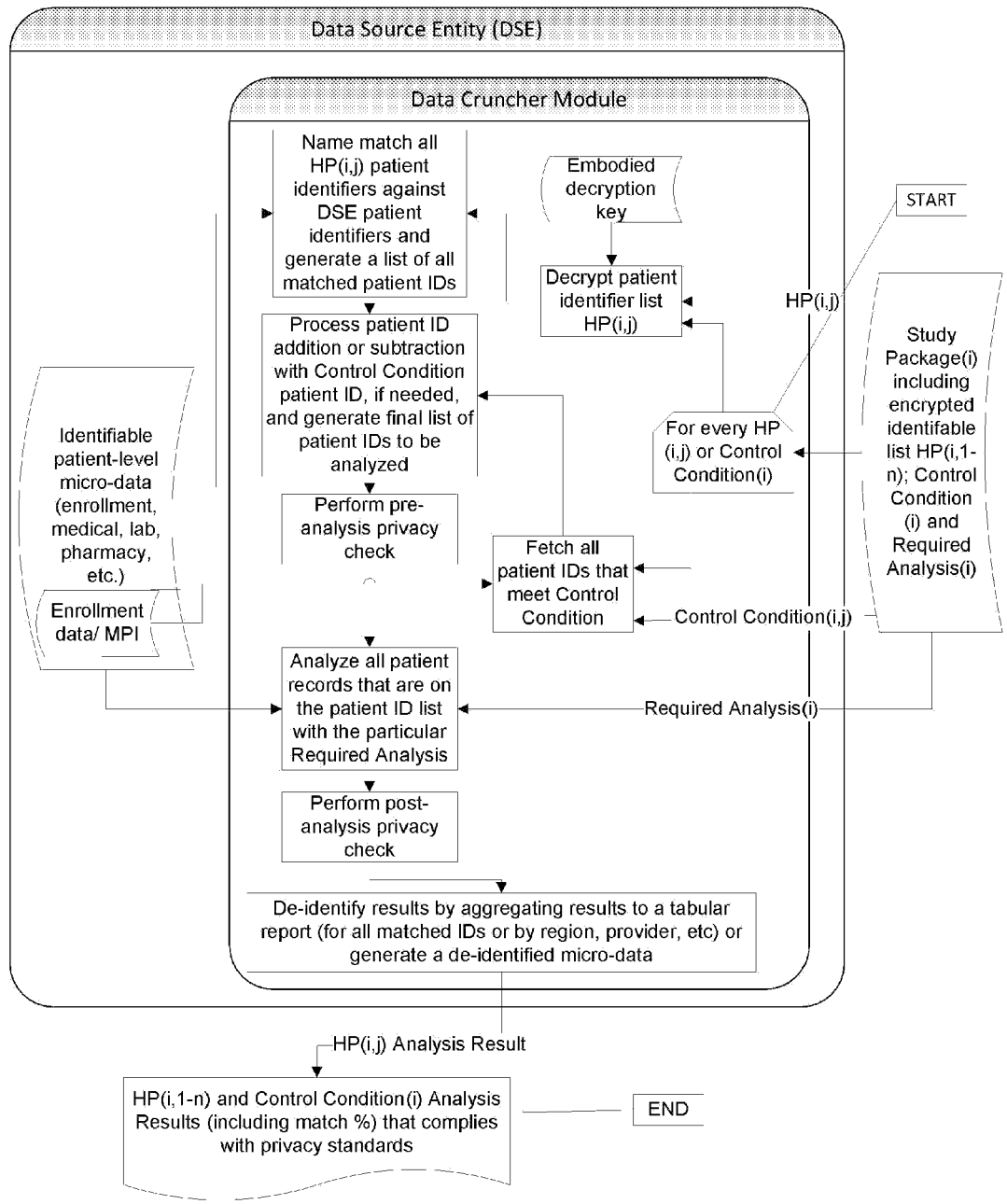
Figure 6:
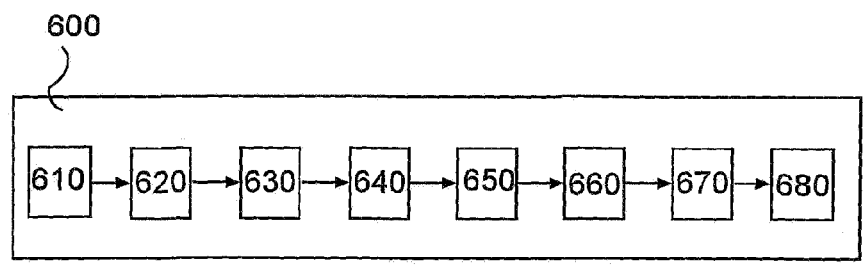
FIGS. 6 & 7 illustrate schematic views of program storage devices respectively having a portion of the instant protocol thereat.
Figure 7:
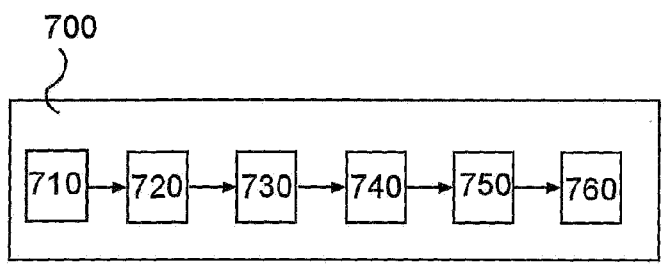
Figure 8:
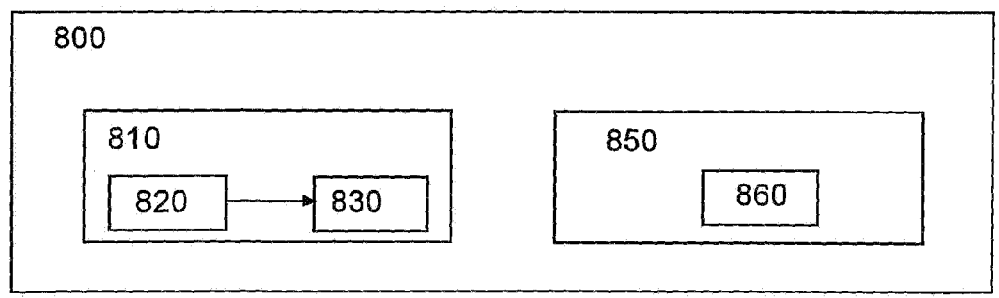

By contrast, an example of "classic" model of health analytics calls for aggregation of de-identified patient-level or physician-level data which allow the central analysis model only (see FIGS. 1 & 2). The common method used by existing healthcare analytics companies (such as IMS, NDCHealth and Verispan) is based on the following steps: (A) De-identify & Aggregate—patient data is de-identified (some data is removed or grouped together) and data is reported typically at the physician level. In some cases the dataset includes longitudinal de-identified patient-level data (such as Verispan and Dendrite) (B) Collect from various sources—data is collected from multiple healthcare organizations into a data warehouse (C) Analyze—syndicated data reports and custom studies are produced.

The instant Crossix "method" is based on an opposite sequence: (A) Analyze—the healthcare organization (such as health plan) runs an analysis software that receive as an input the required analysis and aggregation level as well as possibly a list of identifiable patients or physicians for which analysis is requested. This analysis is performed on the original, most complete data set; (B) De-identify & Aggregate—Once name matching and analysis is complete data is aggregated and, if needed, de-identified; (C) and Collect from various sources—Analysis responses from multiple organization are composed to deliver the analyses requested.

Final Notices: Firstly, it should be appreciated that embodiments of the instant invention relate to the protocol as a whole, individually to respective aspects operating on an "aggregator" processor and on a "source-entity" processor; to specific configurations of computer readable software for allowing either processor to execute characterizing steps of the protocol, and to memory media having any of said software encoded therein; wherein the memory media includes physical media—such as magnetic or optical disks, read only memory and the likes, and to virtual media—such as downloadable execution code data transmission and the likes. Finally, while the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

I claim:

1. A Privacy Preserving Data-Mining Protocol, operating between a secure "aggregator" data processor and at least one of "source-entity" data processor, wherein the "aggregator" and the "source-entity" processors are interconnected via an electronic data-communications topology, and the protocol includes the steps of:
    A) on the side of the "aggregator" processor:
        (i) from a user interface—accepting a query against a plurality of the predetermined attributes and therewith forming a parameter list,
        (ii) via the topology—transmitting the parameter list to each of the "source-entity" processors,
        (iii) via the topology—receiving a respective file from each of the "source-entity" processors,
        (iv) aggregating the plurality of files into a data-warehouse,
        (iv) using the parameter list, extracting query relevant data from the data-warehouse,
        (vi) agglomerating the extract, and
        (vii) to a user interface—reporting the agglomerated extract; and
    B) on the side of each processor of the at least one "source-entity" processors:
        (i) accumulating data-items wherein some of the data-items have privacy sensitive micro-data,
        (ii) organizing the data-items using the plurality of predetermined attributes,
        (iii) via the topology—receiving a parameter list from the "aggregator" processor,
        (iv) forming a file by "crunching together" the data-items according to the parameter list,
        (v) filtering out portions of the file which characterize details particular to less than a predetermined quantity of micro-data-specific data-items, and
        (vi) via the topology—transmitting the file to the "aggregator" processor.

2. The Privacy Preserving Data-Mining Protocol according to claim 1 wherein transmitting the parameter list includes transmitting a sufficiently large list of identity disclosing specifics.

3. The Privacy Preserving Data-Mining Protocol according to claim 1 wherein agglomerating the extract includes filtering out portions of the extract which characterize details particular to less than a predetermined quantity data-items.

4. The Privacy Preserving Data-Mining Protocol according to claim 3 wherein filtering out portions of the extract which characterize details particular to less than a predetermined quantity data-items includes the predetermined quantity being selected from the list, ordinal number, percentage of instances in the data-warehouse, data instances outside of mean plus predetermined number of standard distribution units.

5. The Privacy Preserving Data-Mining Protocol according to claim 1 wherein agglomerating the extract includes filtering out portions of the extract so that only identity-free micro-data remains.

6. The Privacy Preserving Data-Mining Protocol according to claim 1 wherein accepting a query includes performing a preprocessing privacy check against a predetermined source-entity data-ensemble model.

7. The Privacy Preserving Data-Mining Protocol according to claim 1 wherein "crunching together" the data-items includes joining data-items having a mutual micro-data-specific.

8. The Privacy Preserving Data-Mining Protocol according to claim 1 wherein, selected from the list of sub-steps aggregating, extracting, agglomerating, accumulating, organizing, and crunching, at least one sub-step includes fuzzy matching.

9. The Privacy Preserving Data-Mining Protocol according to claim 1 wherein filtering out portions of the file which characterize details particular to less than a predetermined quantity of micro-data-specific data-items includes selecting the predetermined quantity from the list, an ordinal number, a percentage of instances in the data-warehouse, data instances outside of statistical mean-or-median plus-and/or-minus a predetermined number of standard deviation units.

10. The Privacy Preserving Data-Mining Protocol according to claim 1 wherein accepting a query includes transforming the query into a standardized query—capable of resulting in a syndicated reporting of the agglomerated extract.

11. A non-transitory program storage device readable by machine, tangibly embodying a program of instructions executable by the machine to perform method steps for "aggregator" data processor functions in a Privacy Preserving Data-Mining Protocol, said method steps including:
   (i) from a user interface—accepting a query against a plurality of the predetermined attributes and therewith forming a parameter list,
   (ii) via an electronic data-communications topology—transmitting the parameter list to at least one "source-entity" processors,
   (iii) via the topology—receiving a respective file from each of the "source-entity" processors,
   (iv) aggregating the plurality of files into a data-warehouse,
   (v) using the parameter list, extracting query relevant data from the data-warehouse,
   (vi) agglomerating the extract, and
   (vii) to a user interface—reporting the agglomerated extract.

12. A non-transitory program storage device readable by machine, tangibly embodying a program of instructions executable by the machine to perform method steps for "source-entity" data processor functions in a Privacy Preserving Data-Mining Protocol, said method steps including:
   (i) accumulating data-items wherein some of the data-items have privacy sensitive micro-data,
   (ii) organizing the data-items using the plurality of predetermined attributes,
   (iii) via an electronic data-communications topology—receiving a parameter list from an "aggregator" processor,
   (iv) forming a file by "crunching together" the data-items according to the parameter list,
   (v) filtering out portions of the file which characterize details particular to less than a predetermined quantity of micro-data-specific data-items,
   (vi) via the topology—transmitting the file to the "aggregator" processor.

* * * * *